US006724473B2

(12) United States Patent
Leong et al.

(10) Patent No.: US 6,724,473 B2
(45) Date of Patent: Apr. 20, 2004

(54) METHOD AND SYSTEM USING EXPOSURE CONTROL TO INSPECT A SURFACE

(75) Inventors: Jenn-Kuen Leong, Cupertino, CA (US); Guoheng Zhao, Milpitas, CA (US); Mehdi Vaez-Iravani, Los Gatos, CA (US)

(73) Assignee: KLA-Tencor Technologies Corporation, San Jose, CA (US)

( * ) Notice: Subject to any disclaimer, the term of this patent is extended or adjusted under 35 U.S.C. 154(b) by 0 days.

(21) Appl. No.: 10/113,145

(22) Filed: Mar. 27, 2002

(65) Prior Publication Data

US 2003/0223058 A1 Dec. 4, 2003

(51) Int. Cl.$^7$ ................................................ G01N 21/00
(52) U.S. Cl. .................................. 356/237.2; 356/237.4
(58) Field of Search ........................... 356/237.1–237.4; 250/492.1, 492.2; 382/145–152

(56) References Cited

U.S. PATENT DOCUMENTS

| | | | | |
|---|---|---|---|---|
| 4,300,122 A | * | 11/1981 | McMahon | 382/147 |
| 4,301,471 A | * | 11/1981 | Holscher et al. | 348/155 |
| 4,578,810 A | * | 3/1986 | MacFarlane et al. | 382/147 |
| 4,811,410 A | * | 3/1989 | Amir et al. | 382/147 |
| 6,400,454 B1 | * | 6/2002 | Noguchi et al. | 356/237.3 |
| 6,411,377 B1 | * | 6/2002 | Noguchi et al. | 356/237.4 |
| 6,437,312 B1 | * | 8/2002 | Adler et al. | 250/216 |
| 6,556,290 B2 | * | 4/2003 | Maeda et al. | 356/237.2 |

FOREIGN PATENT DOCUMENTS

WO    WO 99/06823    2/1999

* cited by examiner

*Primary Examiner*—Michael P. Stafira
(74) *Attorney, Agent, or Firm*—Parson Hsue & De Runtz LLP (57) ABSTRACT

A method and system of using exposure control to inspect a surface, such as a wafer. One inspection system comprises charge coupled devices (CCDs) as detectors. The exposure control function of each CCD is used to adjust integration times on individual taps of the CCD such that light scattered from the surface, which may contain multiple scattering regions, is within a dynamic range of the CCD during inspection.

53 Claims, 5 Drawing Sheets

METHOD AND SYSTEM USING EXPOSURE CONTROL TO INSPECT A SURFACE

INCORPORATION BY REFERENCE

Co-assigned PCT patent application Ser. No. PCT/US98/16116, filed on Jul. 28, 1998 and published on Feb. 11, 1999, is hereby incorporated by reference in its entirety.

BACKGROUND OF THE INVENTION

1. Field of the Invention

The present invention relates to a surface inspection system, such as a wafer inspection system. Specifically, the present invention relates to a method of using exposure control to improve defect sensitivity across the surface, which may contain multiple scattering regions.

2. Background of the Invention

Traditionally, there have been two scattering-based, patterned-wafer inspection systems: a laser spot scanning system and a flood-illumination imaging system. In general, the sensitivity of a system depends on three fundamental system parameters in patterned-wafer inspection, which comprise (1) spatial resolution, (2) Fourier filtering and (3) multi-channel filtering. Fourier filtering eliminates the repetitive or periodic scattering light intensity patterns from the wafer, and multi-channel filtering discriminates the shape of patterns from the wafer. The advantages of the laser spot scanning system are multi-channel filtering capability and Fourier filtering on the array, when the cell size is smaller than the spot size. The advantages of the flood-illumination imaging system are high spatial resolution and effective Fourier filtering capability.

SUMMARY OF THE INVENTION

Recently, aspects of a laser spot scanning system and a flood-illumination imaging system have been successfully combined in a "line-illumination imaging system" (i.e., a hybrid system), as described in co-assigned PCT patent application Ser. No. PCT/US98/16116, filed on Jul. 28, 1998 and published on Feb. 11, 1999, which is hereby incorporated by reference in its entirety. The line-illumination imaging system provides spatial resolution that satisfies today's desired market requirements and future market requirements, and retains Fourier filtering and multi-channel filtering capabilities.

In addition to the sensitivity of a wafer inspection system, high throughput may also be desired. The throughput of a system depends on the data rate of the system. A spot scanning system may use a Photo Multiplier Tube (PMT) for detection. A flood-illumination may use Time Delay Integration (TDI) for detection. A line-illumination imaging system may use one or more line-scan Charge Couple Devices (CCDs) for detection. A PMT processes one data point at a time, but a TDI or a CCD may process several data points simultaneously. Therefore, the data rates (and thus throughput) for a flood-illumination with TDI and a line-illumination system with CCD are usually higher than that of a spot scanning system with PMT.

Other than the system parameters described above, not utilizing the full dynamic range of a detector on some regions of the wafer during inspection can penalize detection sensitivity. The "dynamic range" of a detector is the range between minimum and maximum detectable light of the detector. The scattering intensity of a pattern depends on many factors, such as for example, local wafer structures, illumination angle, illumination polarization, illumination wavelength, illumination line width, collection angle, collection polarization, and numerical aperture (NA) of a collector. Collection NA is the sine of the half angle of the cone of collection in this application. Within a die, there are random (logic) structures and array patterns. The logic structures scatter randomly, and the array structures scatter periodically. The periodic array patterns can be blocked out using Fourier filters, and the remaining scatter light intensity signal should be caused by defects. Therefore, the scattering light intensity may differ significantly from region to region within a die.

In order to obtain good sensitivity across the wafer, the scattering intensity collected by the detector should to be within a certain dynamic range or limit. If the scattering intensity is too strong, it will saturate the detector and give false counts after die-to-die or cell-to-cell comparison. If the scattering intensity is too low, a scattering light intensity signal caused by a defect on the wafer may be too weak to overcome the electronic noise after die-to-die or cell-to-cell comparison, and results in lost sensitivity. Therefore, the upper limit of the detector is determined by detector saturation, and the lower limit is determined by electronic noise.

Traditionally, the power of the laser and the integration time (time period to collect light) of the detector are fixed during inspection. Therefore, it is difficult to guarantee that all scattering intensities coming out of the wafer are within a certain dynamic range, and the system may lose sensitivity on some regions. To solve this issue, either the laser power or the detector's integration time should change during inspection. It may not be practical to change the laser power due to the need for high-speed switching and other problems.

A method and system using exposure control to inspect a surface, such as a wafer, is provided in accordance with the present invention. This method utilizes the full dynamic range of a detector and provides good defect sensitivity across the surface, which contains uneven light scattering regions. In one embodiment, this method is implemented by a line-illumination imaging system with CCDs for detection.

The invention described above may be used to provide a viable alternate mechanism to inspect patterned or unpatterned wafers, photomasks, reticles, liquid crystal displays and other flat panel displays. Also, this invention may be used for any inspection system that uses CCDs for detection.

One aspect of the invention relates to a system configured to inspect a surface, such as a wafer. The surface comprises at least two regions that scatter light differently. The system comprises a charge coupled device (CCD) configured to collect light scattered from the surface. The CCD comprises a plurality of taps. Each tap comprises a set of pixels. The CCD is configured to independently adjust an integration time of each tap depending on where the set of pixels of the tap is positioned to collect light scattered from the surface.

Another aspect of the invention relates to a charge coupled device (CCD) configured to collect light scattered from a surface, such as a wafer. The surface comprises two regions that scatter light differently. The CCD comprises a plurality of taps. Each tap comprising a set of pixels. The CCD is configured to independently adjust an integration time of each tap depending on where the set of pixels of the tap is positioned to collect light scattered from the surface.

Another aspect of the invention relates to a method of collecting light scattered from a surface, such as a wafer. The surface comprises two regions that scatter light differently. The method comprises setting integration times for a plurality of taps in a charge coupled device (CCD) according to where pixels of the taps are positioned to collect light scattered from the surface; and collecting light scattered from the surface during the integration times.

Another aspect of the invention relates to a method of setting integration times for a plurality of taps in a charge coupled device (CCD). The CCD is configured to scan a surface, such as a wafer, comprising two regions that scatter light differently. The method comprises setting a first integration time for a first tap positioned to collect light scattered from the first region; setting a second integration time for a second tap positioned to collect light scattered from the second region, wherein the first integration time is different than the second integration time; and collecting light scattered from the first and second regions.

In one embodiment, collection optics are arranged such that radiation scattered from different parts of a line illuminated by a beam from a laser is imaged onto different pixels (and thus taps) of the same CCD.

DETAILED DESCRIPTION

Line-Illumination System

In a line-illumination system, a laser illuminates the wafer surface in a shape of a line. The illumination line preferably has a very narrow width, such as about 1–3 microns or less for example, and a relatively long length, such as about 0.1 to about 10 mm or longer for example. The narrow width of the illumination line has advantages of a spot scanning system and allows multiple inclined imaging systems, e.g., collectors 117–119 in FIGS. 1 and 2, to provide multi channel filtering capability. On the other hand, the long length of the illumination line has advantages of a flood-illumination system and provides effective Fourier filtering.

Figure 1:
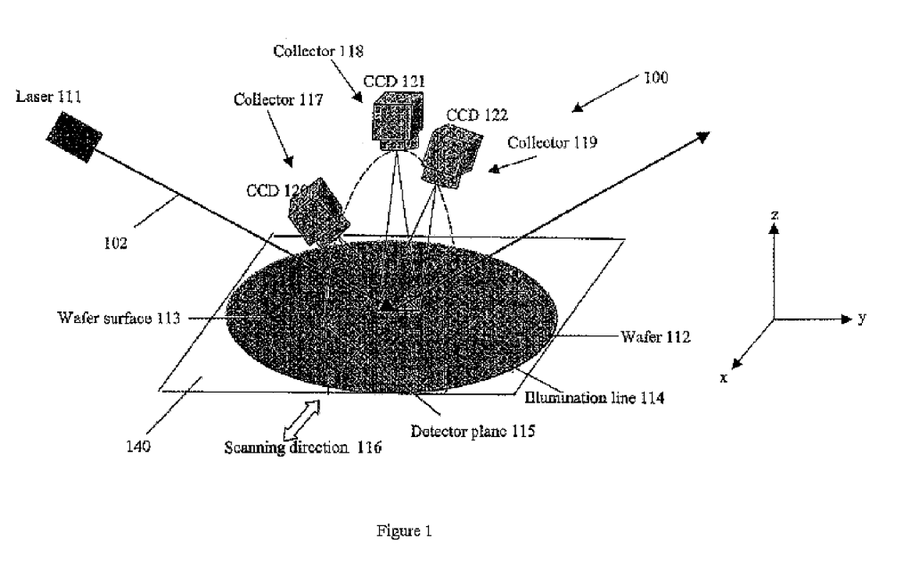
FIG. 1 illustrates one embodiment of a line-illumination inspection system with oblique illumination.
Figure 2:
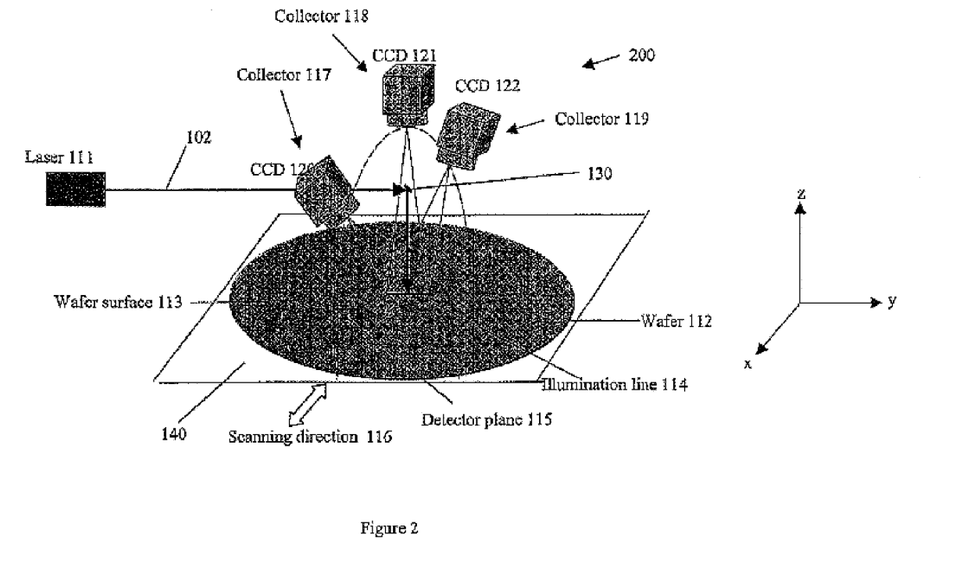
FIG. 2 illustrates one embodiment of a line-illumination inspection system with normal illumination.

The angle of illumination may be either oblique or normal. FIG. 1 illustrates one embodiment of a line-illumination inspection system 100 with oblique illumination. FIG. 2 illustrates one embodiment of a line-illumination inspection system 200 with normal illumination. The system 100 in FIG. 1 comprises a laser 111 and collectors 117–119, which comprise detectors 120–122, such as charge coupled devices (CCDs). The system 100 may further comprise collection and/or illumination optics (not shown), such as one or more lenses, mirrors, beam splitters, beam expanders, polarizers, and wave plates. Various aspects of the system 100 are described in co-assigned PCT patent application Ser. No. PCT/US98/16116, which has been incorporated by reference. A laser 111 in FIG. 2 generates a laser beam 102 that reflects off a mirror 130 to be incident on the wafer surface 113. The system 200 may further comprise collection and/or illumination optics (not shown), such as one or more lenses, mirrors, beam splitters, beam expanders, polarizers, and wave plates.

The laser 111 in FIGS. 1 and 2 may comprise any type of laser. The laser 111 may emit radiation with any desired power and wavelength, such as for example, 532 nm, 355 or 266 nm. The laser 111 generates a laser beam 102 that passes through illumination optics (not shown in FIGS. 1 and 2) and illuminates a wafer surface 113 in the shape of a line 114. The illumination line 114 may be generated by illumination optics. The illumination line 114 is perpendicular to the detector plane 115 and also perpendicular to a scanning direction 116 of the wafer 112.

The description below may refer to the system 100 in FIG. 1, but the description below may also be applied to the system 200 in FIG. 2.

In FIGS. 1 and 2, the wafer 112 is placed on a stage 140 that is configured to move the wafer 112. The wafer 112 is scanned by moving the stage 140 in a scanning direction, which is perpendicular to an illumination line, such that the illumination line 114 scans the wafer surface 113. For example, the wafer 112 may be moved in a scanning direction indicated by an arrow 116. The wafer surface 113 scatters light from the wafer due to the line-illumination 114. The scattered light is collected by the collectors 117–119 and imaged on the CCDs 120–122 of the collectors 117–119. The collectors 117–119 in FIGS. 1 and 2 may comprise lenses, Fourier filters, polarizers and detectors. The detectors 120–122 used in this system are linear charge coupled devices (CCDs)(also called line-scan CCDs). All CCDs 120–122 are in a detector plane 115, which is perpendicular to the illumination line 114, as shown in FIGS. 1 and 2.

Like a TDI system, a linear CCD can process several data points simultaneously. Since all detectors 120–122 in FIGS. 1 and 2 are linear CCDs, the throughput of the systems 100, 200 can be very high. In one embodiment, each CCD is a linear CCD that processes about one gigabyte of data per second. In other embodiments, each CCD may process less than or more than one gigabyte of data per second. The data rate for a CCD can be designed according to desired throughput of the system.

The systems 100, 200 may each comprise less than three or more than three collectors. Also, the systems 100, 200 may comprise both oblique and normal illumination.

CCD and Exposure Control

Figure 3:
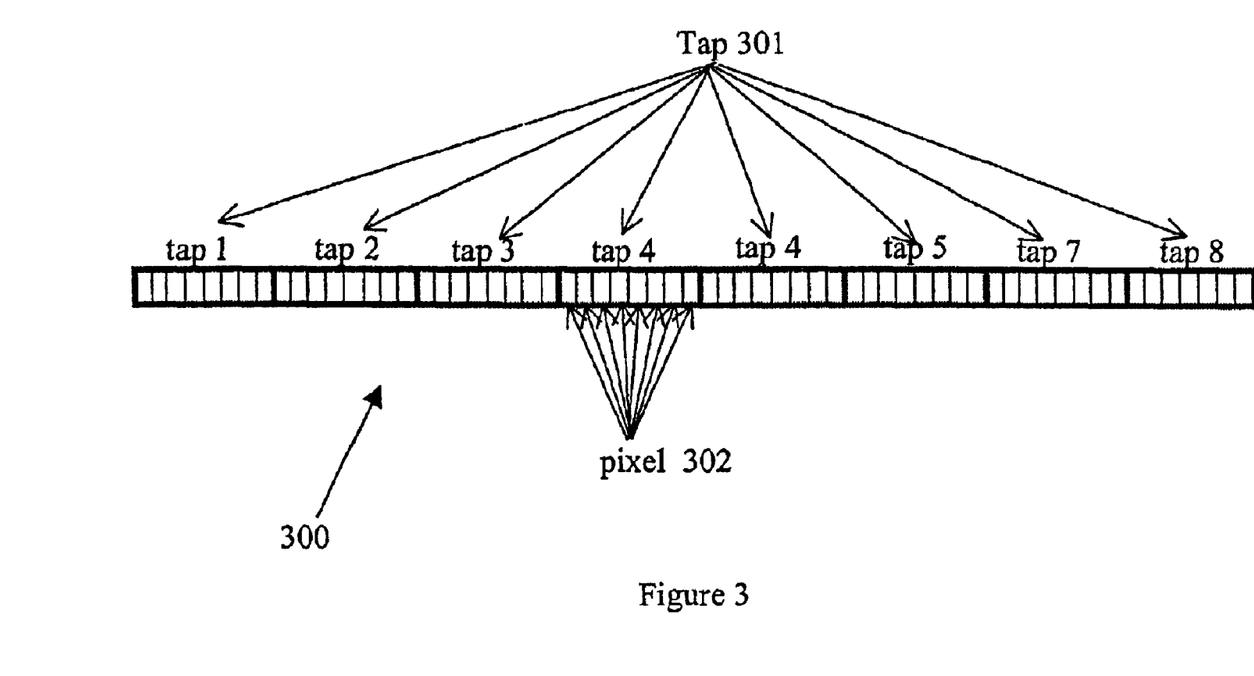
FIG. 3 illustrates an example of a charge couple device (CCD) that may be used in FIGS. 1 and 2.

FIG. 3 illustrates an example of a CCD 300 that may be used in the systems 100, 200 of FIGS. 1 and 2. In one embodiment, the CCD 300 in FIG. 3 is a one-dimensional array sensor, having a line of pixels. Most CCD applications use 512, 1024, 2048, or 4096 pixels, but a CCD may have any desired number of pixels. The CCD 300 in FIG. 3 has 64 pixels. The CCD 300 may also have several taps 301. A "tap" is a group of pixels. Pixels within a tap are read out serially, but taps are read out in parallel such that the data rate of the CCD is higher. The CCD 300 in FIG. 3 has 8 taps 301, where each tap controls 8 pixels 302. The CCD for an actual inspection system may have any number of pixels and taps. More taps may be better for a line-illumination inspection system, but it may require a complex camera design.

Each tap controls the integration time for a set of pixels. "Integration time" is a time period within which a pixel collects light. A CCD in accordance with the invention allows integration time to be changed on a tap-by-tap basis with a very fast speed, i.e., the CCD can independently control the integration time for each tap. As an example, such CCDs may be obtained from DALSA Digital Imaging Solutions in Waterloo, Ontario, Canada or from PerkinElmer Optoelectronics in Santa Clara, Calif., by custom order.

Even though such CCDs are different from those available commercially, the CCD designer or CCD maker would understand how to modify the traditional CCD design to allow integration times to be set and changed on a tap-by-tap basis.

A CCD may have a variable line rate and gain. CCD gain is a function of the amplifier that converts the electrons collected by each pixel to a form of electrical signal (normally voltage) that can be readout and digitized.

A short integration time lets pixels collect less light, and a longer integration time lets pixels collect more light. The integration times on pixels within a tap are the same, but the integration times on pixels within different taps may be different. Changing CCD integration time on tap-by-tap basis may be called "exposure control." This exposure control of the CCD allows the line-illumination inspection system, such as systems 100, 200, to provide the scattering signal across the wafer within the dynamic range described above.

Ideally, continuous variation of the integration time on every tap from 0 to the 1/(CCD line rate) is desired. The "CCD line rate" is the number of times per second that a linear CCD can be read. Practically, varying the integration time by some percent (1%, 2%, ... up to 100%) of 1/(CCD line rate) is sufficient for a line-illumination inspection system, such as systems 100, 200.

The collection optics (not shown in FIGS. 1 & 2) in collectors 117–119 project an image of a portion of the illuminated line 114 onto corresponding pixels (and thus taps) in the CCD array 120–122 such that each pixel detects scattering light from a corresponding portion of the illuminated line 114. Therefore, light scattering from different parts of the illuminated line 114 (and thus different scattering regions) is imaged onto different pixels (and thus different taps) of each CCD. More details are described in co-assigned PCT patent application Ser. No. PCT/US98/16116, which has been incorporated by reference.

One principle of the line-inspection systems 100, 200 described herein is to achieve a good scattering light intensity signal that uses the maximum (non-saturated) gray level from all regions across a wafer by setting different CCD integration times on different regions.

In one embodiment, collection optics are arranged such that radiation scattered from different parts of the illumination line 114 (FIGS. 1 and 2) from the laser beam 102 is imaged onto different taps 301 (FIG. 3) of the same CCD.

Manual Exposure Control

In manual exposure control, the inspection system needs to know exact locations of different light scattering regions such that the system can apply different CCD integration times on different regions.

One of the most useful applications of the systems 100, 200 is inspecting a wafer containing array and logic structures since array and logic patterns scatter differently. Logic patterns in a logic region scatter light randomly, and array patterns in an array region scatter light periodically. Periodic scattering patterns from array regions can be filtered out using Fourier filters on a Fourier plane of the collector. After Fourier filtering of array patterns, the array region appears much darker than the logic region in scattering images. During inspection, the illumination laser power is fixed. If the laser power is set such that the scattering from a logic region is within the dynamic range of the CCD, the scattering from a filtered array region may be weak, and electronic noise of the CCD may dominate the array region. If the laser power is set such that the scattering from filtered array regions is within the dynamic range of the CCD, the scattering from a logic region may be strong and saturate the CCD. Both situations will not provide the scattering signal from both logic and filtered array regions within a dynamic range of the CCD and may lose defect sensitivity after die-to-die or cell-to-cell comparison. In order to avoid losing sensitivity, CCD integration time on logic and array regions can be set differently.

Figure 4:
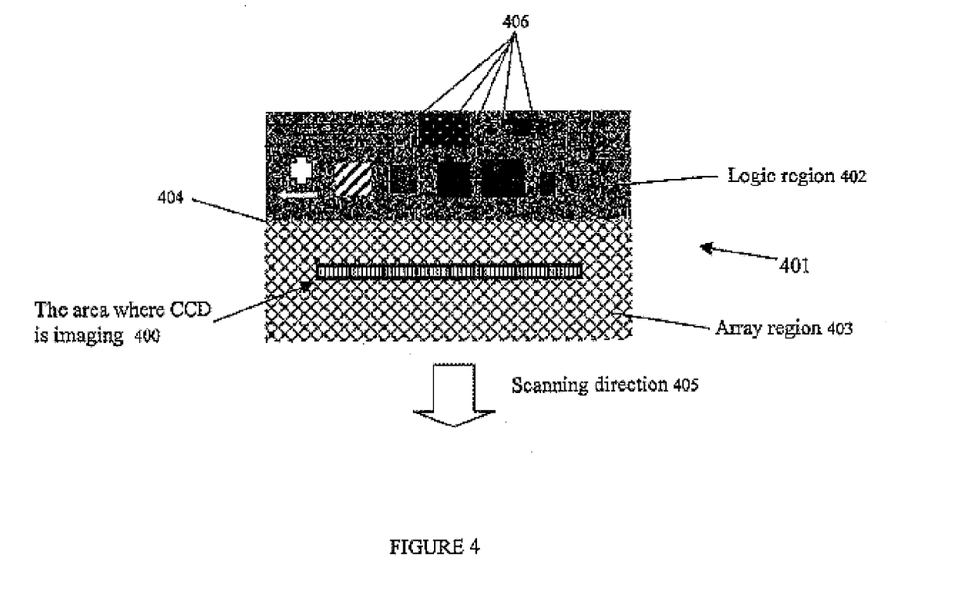
FIG. 4 illustrates one embodiment of a CCD field of view that is configured to scan a wafer that is moved in a direction perpendicular to an illumination line, such as a direction indicated by a scanning direction arrow.

FIG. 4 illustrates one embodiment of a CCD field of view 400 on a wafer 401. The wafer 401 comprises an array region 403 and a logic region 402, which may comprise a plurality of logic structures 406. The CCD field of view 400 sees only array region 403 or only logic region 402 when the wafer 401 is scanned from one region to another region. The wafer 401 may be moved in a scanning direction perpendicular to an illumination line, such as the arrow 405 shown in FIG. 4.

In one embodiment, the CCD 400 examines the array region 403 and then the logic region 402 or vice versa. After applying Fourier filters on the collection path to filter out periodic array patterns, the array region 403 appears much darker than the logic region 402 in scattering images. Since the power of an illumination laser is fixed during inspection, two different CCD integration times are set for the different regions 402, 403 in order to avoid losing sensitivity. Generally, a relatively longer integration time is desired when the CCD scans the filtered array region 403, and a relatively shorter integration time is desired when the CCD scans the logic region 402.

There are many ways to set CCD integration times for these regions 402, 403 before inspection such that the scattering light intensity signals from these regions 402, 403 are within a dynamic range of the CCD during inspection. The following is one example of setting the laser power and integration time on the CCD before inspection. For a given CCD line rate, a relatively long integration time is set on the CCD during inspection of the filtered array region 403, and the laser power is tuned until a (non-saturated) maximum gray level is achieved by the CCD. Then the laser power is fixed, and the CCD examines the logic region 402 as the wafer 401 is moved. The CCD integration time is reduced such that the CCD obtains a (non-saturated) maximum gray level from the logic region 402. In this example, the CCD integration times on the array and logic regions 403, 402 are different, but the integration times on all taps of the CCD are the same for each region.

The location of the boundary 404 between the array and logic regions 403, 402 should be programmed in or considered by the inspection system in order to switch the integration time upon crossing the border 404.

Figure 5:
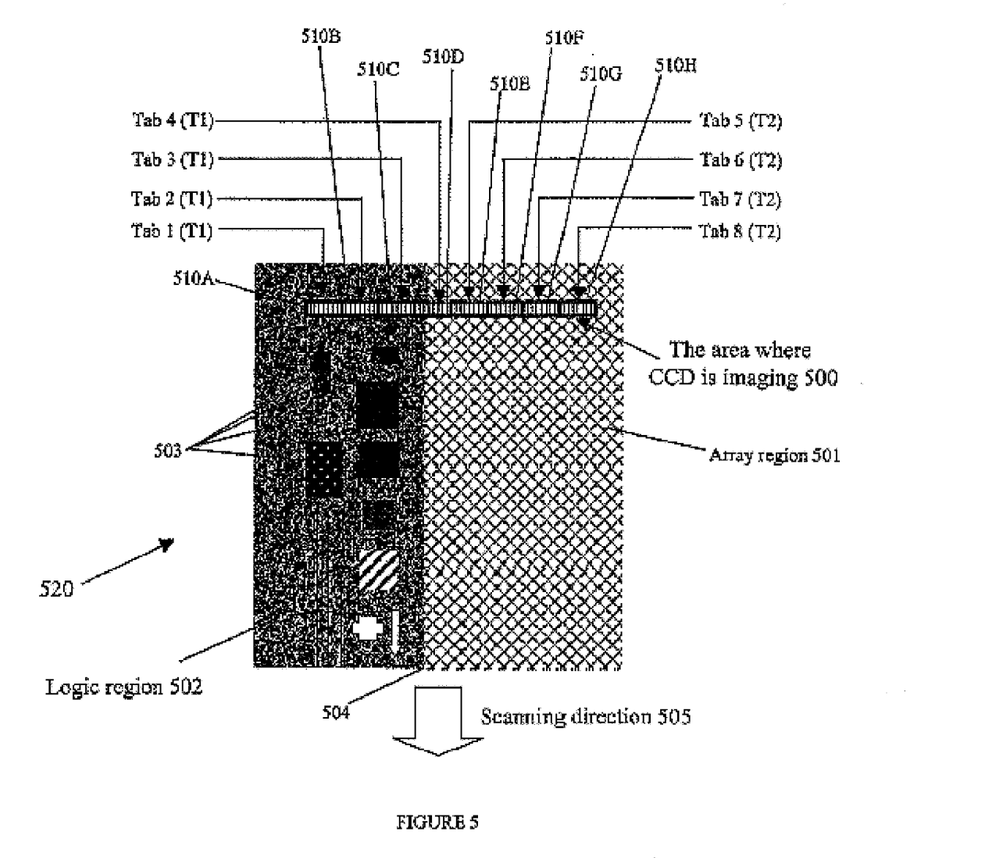
FIG. 5 illustrates one embodiment of another CCD field of view that is configured to scan a wafer that is moved in a direction perpendicular to an illumination line, such as a direction indicated by a scanning direction arrow.

FIG. 5 illustrates another situation of inspecting array and logic regions 501, 502. FIG. 5 illustrates one embodiment of a CCD field of view 500 configured to scan a wafer 520 that is moved in a direction perpendicular to an illumination line, such as a direction indicated by a scanning direction arrow 505. In FIG. 5, both array and logic regions 501, 502 lie in the same CCD field of view 500. The CCD 500 can simultaneously inspect both regions 501, 502. The CCD 500 has eight taps 510A–510H, wherein each tap is coupled to eight pixels. The logic region 502 may comprise a plurality of logic structures 503. The array scattering patterns may be filtered out using Fourier filter. Since both array and logic regions 501, 502 are in the same field of view 500, the CCD may apply different integration times on individual taps 510A–510H. In FIG. 5, the taps 510E–510H cover only the array region 501, and the taps 510A–510C cover only the logic region 502. The taps 510E–510H may be set with a different integration time than taps 510A–510C. The boundary 504 (between array region 501 and logic region 502) is covered by the tap 510D.

There are many ways to set the CCD integration times on these regions 501, 502 before inspection such that the scattering signals from these regions 501, 502 are within a dynamic range of the CCD during inspection. The following is one example of setting the laser power and integration time on the CCD before inspection. As in the example describe above with FIG. 4, the laser power and the CCD integration time on filtered array region 501 are set first, and then CCD integration time on the logic region 502 is set.

For the tap 510D covering the boundary (between array and logic region), a default integration time may be set. For example, the default integration time for this tap may be set to the smaller integration time of these two regions 501, 502. A user may set this value different than the default value. If the integration time for the logic region 502 is selected for this tap 510D, the array sensitivity may be compromised. On the other hand, if integration time for the array region 501 is selected, the logic sensitivity may be compromised. Therefore, a compromise in sensitivity has to be made in those cases where mixed logic and array pattern coexists in a given tap. To minimize losing sensitivity on the boundary 504 between the two scattering regions 501, 502, the CCD may be designed with more taps, and each tap contains a smaller numbers of pixels.

In FIG. 5, the first, second and third taps 510A–510C cover only the logic region 502, and their integration times may be set to a time T1. The fifth through eighth taps 510E–510H cover only the array region 501, and their integration times may be set to a time T2. The fourth tap 510D covers both array and logic regions 501, 502 and its integration time may be set to a time T1. Since Fourier filtering is applied to the array region 501, T1 is smaller than T2, and T2 is smaller than 1/ (a given line rate of the CCD).

This exposure control can be applied to cases where multitude of scattering characteristic exists on a given wafer. For various logic regions, scattering can be stronger in one logic region compared to another logic region. The same is true for different array regions. The background scattering is different from one array region to the other array region after applying Fourier filtering. As long as the inspection system knows exact locations of these regions, the system can apply different exposure control on these regions. This exposure control can be applied not only to scattering-based (dark field) but also to reflection-based (bright field) wafer-inspection systems.

Auto Exposure Control

The embodiments described above use manual exposure control since the inspection system should know the exact locations of different scattering regions. Another way of addressing the issue of utilizing a full dynamic of the CCD is using automatic exposure control, which will automatically adjust the integration time on tap-by-tap basis. If the scattering intensity is too strong, the CCD may reduce the integration time such that the CCD reaches a predefined gray level. On the other hand, if the scattering intensity is too weak, the CCD may increase the integration time such that the CCD reaches a predefined gray level. One advantage of this automatic exposure control method is that the inspection system does not need to know exact locations of different scattering regions. One disadvantage is that there is image lag between old and new gray levels.

The invention described above may be used to provide a viable alternate mechanism to inspect patterned or unpatterned wafers, photomasks, reticles, liquid crystal displays and other flat panel displays. Also, this invention may be used for any inspection system that uses CCDs for detection.

In summary, one embodiment of the line-illumination inspection system described herein comprises CCDs as detectors, in which the exposure control function of each CCD utilizes a full dynamic range of the CCD across the wafer during inspection.

The above-described embodiments of the present invention are merely meant to be illustrative and not limiting. Various changes and modifications may be made without departing from the invention in its broader aspects. The appended claims encompass such changes and modifications within the spirit and scope of the invention.

What is claimed is:

1. A system configured to inspect a wafer, the wafer comprising at least two regions that scatter light differently, the system comprising:
   a collector configured to collect light scattered from the wafer, the collector comprising a charge coupled device (CCD), the CCD comprising:
      a plurality of taps, each tap comprising a set of pixels, the CCD being configured to independently adjust an integration time of each tap depending on where the set of pixels of the tap is positioned to collect light scattered from the wafer, wherein the integration times of at least two taps positioned to collect light scattered from the at least two regions are different.

2. A system configured to inspect a wafer, the wafer comprising at least two regions that scatter light differently, the system comprising:
   a colletor configured to collect light scattered from the wafer, the collector comprising a charge couple device (CCD), the CCD comprising:
      a plurality of taps, each tap comprising a set of pixels, the CCD being configured to independently adjust an integration time of each tap depending on where the set of pixels of the tap is positioned to collect light scattered from the wafer, wherein the wafer comprises a first region that scatters light substantially randomly, and a second region that scatters light substantially periodically.

3. The system of claim 1, wherein the CCD is configured to set an integration time of a tap with pixels that collect light scattered from a region with logic structures.

4. The system of claim 1, wherein the CCD is configured to set an integration time of a tap with pixels that collect light scattered from a region with array structures.

5. The system of claim 1, further comprising a Fourier filter configured to block periodic scattering light intensity.

6. The system of claim 1, being configured to use a full dynamic range of the CCD across the wafer during inspection.

7. The system of claim 1, being configured to use a maximum non-saturated, gray level of the CCD as the inspection system scans the wafer.

8. The system of claim 1, wherein the CCD is a linear CCD.

9. The system of claim 1, wherein the CCD is configured to simultaneously change integration times of two or more taps.

10. A system configured to inspect a wafer, the wafer comprising at least two regions that scatter light differently, the system comprising:
    a collector configured to collect light scattered from the wafer, the collector comprising a charge coupled device (CCD), the CCD comprising:
       a plurality of taps, each tap comprising a set of pixels, the CCD being configured to independently adjust an integration time of each tap depending on where the set of pixels of the tap is positioned to collect light scattered from the wafer, the system being configured to allow a user to manually adjust the integration time of each tap depending on where the set of pixels of the tap is collecting light scattered from the wafer.

11. A system configured to inspect a wafer, the wafer comprising at least two regions that scatter light differently, the system comprising:

a collector configured to collect light scattered from the wafer, the collector comprising a charge coupled device (CCD), the CCD comprising:

a plurality of taps, each tap comprising a set of pixels, the CCD being configured to independently adjust an integration time of each tap depending on where the set of pixels of the tap is positioned to collect light scattered from the wafer, the system being configured to automatically adjust the integration time of each tap depending on where the set of pixels of the tap is collecting light scattered from the wafer.

12. The system of claim 1, wherein the integration time of each tap is set before the system inspects the wafer.

13. The system of claim 1, further comprising a light source configured to generate an illumination line on the wafer, wherein the CCD collects light scattered from the wafer due to the illumination line.

14. The system of claim 13, wherein the collector is positioned such that radiation scattered from different parts of the illumination line is imaged onto different pixels and taps of the CCD.

15. The system of claim 13, wherein the light source is configured to generate the illumination line with an oblique angle of incidence.

16. The system of claim 13, further comprising a mirror configured to reflect light generated by the light source to have an angle of incidence of about 90 degrees with respect to a surface of the wafer and generate the illumination line.

17. The system of claim 13, wherein the illumination line is less than about 4 microns in width.

18. The system of claim 13, wherein the illumination line is about 0.1 to about 10 mm in length.

19. The system of claim 1, further comprising second and third collectors, the collectors being positioned in a plane that is perpendicular to a plane of the wafer.

20. The system of claim 1, further comprising second and third collectors, the collectors being positioned in a plane that is perpendicular to an illumination line projected on the wafer.

21. The system of claim 1, further comprising second and third CCDs, the CCDs being positioned in a plane that is perpendicular to a plane of the wafer.

22. The system of claim 1, further comprising second and third CCDs, the CCDs being positioned in a plane that is perpendicular to an illumination line projected on the wafer.

23. The system of claim 1, being configured to move the wafer as the CCD collects light scattered from the wafer.

24. The system of claim 1, being configured to move the wafer in a direction perpendicular to an illumination line as the CCD collects light scattered from the wafer.

25. A charge coupled device (CCD) configured to collect light scattered from a surface, the surface comprising at least two regions that scatter light differently, the CCD comprising:

a plurality of taps, each tap comprising a set of pixels, the CCD being configured to independently adjust an integration time of each tap depending on where the set of pixels of the tap is positioned to collect light scattered from the surface, wherein the integration times of at least two taps positioned to collect light scattered from the at least two regions are different.

26. A system configured to inspect a surface, the surface comprising at least two regions that scatter light differently, the system comprising:

a charge coupled device (CCD) configured to collect light scattered from the surface, the CCD comprising:

a plurality of taps, each tap comprising a set of pixels, the CCD being configured to independently adjust an integration time of each tap depending on where the set of pixels of the tap is positioned to collect light scattered from the surface, wherein the integration times of at least two taps positioned to collect light scattered from the at least two regions are different.

27. A method of collecting light scattered from a surface, the surface comprising at least two regions that scatter light differently, the method comprising:

setting integration times for a plurality of taps in a charge coupled device (CCD) according to where pixels of the taps are positioned to collect light scattered from the surface, so that the integration times of at least two taps positioned to collect light scattered from the at least two regions are different; and collecting light scattered from the surface during the integration times.

28. The method of claim 27, further comprising moving the surface such that the CCD collects light from a first one of the two regions and then a second one of the two regions of the surface.

29. The method of claim 27, wherein collecting light comprises simultaneously collecting light scattered from both regions.

30. The method of claim 27, further comprising tuning an intensity of light illuminated on the surface as the CCD collects light scattered from the surface.

31. The method of claim 27, wherein the integration times are set manually.

32. A method of collecting light scattered from a surface, the surface comprising at least two regions that scatter light differently, the method comprising:

setting integration times for a plurality of taps in a charge coupled device (CCD) according to where pixels of the taps are positioned to collect light scattered from the surface;

manually adjusting the integration time of an individual tap; and collecting light scattered from the surface during the integration times.

33. The method of claim 27, wherein the integration times are set automatically.

34. A method of collecting light scattered from a surface, the surface comprising at least two regions that scatter light differently, the method comprising:

setting integration times for a plurality of taps in a charge coupled device (CCD) according to where pixels of the taps are positioned to collect light scattered from the surface;

automatically adjusting the integration time of an individual tap; and collecting light scattered from the surface during the integration times.

35. The method of claim 27, wherein the intensity of light illuminated on the surface is tuned until a non-saturated, maximum gray level is achieved by the CCD.

36. A method of collecting light scattered from a surface, the surface comprising at least two regions that scatter light differently, the method comprising:

setting integration times for a plurality of taps in a charge coupled device (CCD) according to where pixels of the taps are positioned to collect light scattered from the surface, wherein the integration times are adjusted such that the CCD obtains a non-saturated, maximum gray level from different light scattering regions of the surface; and collecting light scattered from the surface during the integration times.

37. The method of claim 27, wherein the CCD collects light scattered from different light scattering regions and adjusts scattering light intensity signals within a predetermined range.

38. The method of claim 27, wherein the integration times are set to at least one predetermined value before inspecting the surface.

39. A method of setting integration times for a plurality of taps in a charge coupled device (CCD), the CCD being configured to scan a surface comprising at least two regions that scatter light differently, the method comprising:

setting a first integration time for a first tap positioned to collect light scattered from the first region;

setting a second integration time for a second tap positioned to collect light scattered from the second region, wherein the first integration time is different than the second integration time; and collecting light scattered from the first and second regions.

40. The method of claim 39, further comprising moving the surface.

41. The method of claim 39, further comprising tuning an intensity of light illuminated on the surface as the CCD collects light scattered from the second region.

42. The method of claim 39, further comprising setting a third integration time for a tap positioned to collect light scattered from portions of the first and second regions.

43. The method of claim 39, wherein the integration times are set manually.

44. The method of claim 39, further comprising manually adjusting the integration time of individual tap.

45. The method of claim 39, further comprising automatically adjusting the integration time of individual tap.

46. The method of claim 39, further comprising directing a light beam to illuminate a line on the surface, wherein the collecting collects light scattered from the illuminated line on the surface.

47. The method of claim 46, wherein the collecting images light scattered from different parts of the illuminated line onto different pixels and taps of the CCD.

48. The method of claim 46, wherein the directing directs light to the surface at an oblique angle of incidence.

49. The method of claim 46, wherein the directing directs light to the surface substantially at an angle of incidence of about 90 degrees with respect to the surface.

50. The method of claim 46, further comprising causing relative motion between the light beam and the surface in a direction substantially perpendicular to the illuminated line as the CCD collects light scattered from the wafer.

51. The system of claim 1, wherein the integration times are adjusted such that the CCD obtains a non-saturated, maximum gray level from different light scattering regions of the surface.

52. A system configured to inspect a surface, the system comprising:

a charge coupled device (CCD) configured to collect light scattered from the surface, the CCD comprising:

a plurality of taps, each tap comprising a set of pixels, the CCD being configured to independently adjust an integration time of each tap depending on where the set of pixels of the tap is positioned to collect light scattered from the surface, wherein the integration times of at least two taps positioned to collect light scattered from different regions of the surface are different.

53. A method of collecting light scattered from a surface, the method comprising:

setting integration times for a plurality of taps in a charge coupled device (CCD) according to where pixels of the taps are positioned to collect light scattered from the surface, so that the integration times of at least two taps positioned to collect light scattered from different regions of the surface are different; and collecting light scattered from the surface during the integration times.

* * * * *